United States Patent [19]

Friedman, Jr. et al.

[11] Patent Number: 4,975,109
[45] Date of Patent: Dec. 4, 1990

[54] MICROBIOCIDAL COMBINATIONS OF MATERIALS AND THEIR USE

[75] Inventors: Lester A. Friedman, Jr.; Richard F. McFarlin, both of Atlanta, Ga.

[73] Assignee: Lester Technologies Corp., Atlanta, Ga.

[21] Appl. No.: 189,379

[22] Filed: May 2, 1988

[51] Int. Cl.$^5$ .................... A01N 31/00; A01N 33/00; D21N 21/04; D21N 21/36

[52] U.S. Cl. ....................................... 71/67; 162/161

[58] Field of Search ......................... 71/67; 162/161

[56] References Cited

U.S. PATENT DOCUMENTS

| | | | |
|---|---|---|---|
| 2,374,754 | 1/1945 | Kreidl et al. | 167/14 |
| 2,768,949 | 2/1956 | Hewey | 210/6 |
| 3,248,281 | 2/1966 | Goodenough | 167/17 |
| 3,252,855 | 5/1966 | Wehner et al. | 167/22 |
| 3,306,810 | 2/1967 | Buckman et al. | 162/161 |
| 3,377,275 | 4/1968 | Michalski et al. | 210/64 |
| 3,393,058 | 2/1968 | Oppermann | 44/68 |
| 3,426,134 | 7/1969 | Shema et al. | 424/302 |
| 3,524,812 | 3/1970 | Shema et al. | 210/63 |
| 3,574,697 | 4/1971 | Welcher | 260/454 |
| 3,647,703 | 3/1972 | Shema et al. | 252/180 |
| 3,674,457 | 2/1972 | Wolfson et al. | 71/67 |
| 3,690,860 | 9/1972 | Salutsky et al | 71/67 |
| 3,817,828 | 4/1974 | Bendiner | 162/161 |
| 3,860,713 | 8/1974 | Shema et al. | 424/426 |
| 3,864,053 | 3/1975 | Shema et al. | 210/62 |
| 3,864,253 | 12/1975 | Shema et al. | 210/62 |
| 3,879,559 | 11/1975 | Shema et al. | 424/270 |
| 3,896,229 | 11/1975 | Shema et al. | 424/270 |
| 3,896,231 | 6/1975 | Shema et al. | 424/304 |
| 3,897,554 | 6/1975 | Shema et al. | 424/248 |
| 3,897,562 | 6/1975 | Shema et al. | 424/304 |
| 3,908,030 | 11/1975 | Shema et al. | 424/270 |
| 3,928,198 | 12/1975 | Brink, Jr. et al. | 210/62 |
| 3,929,561 | 12/1975 | Shema et al. | 162/161 |
| 3,929,562 | 12/1975 | Shema et al. | 162/161 |
| 3,929,563 | 12/1975 | Shema et al. | 162/161 |
| 3,930,015 | 12/1975 | Swered et al. | 424/298 |
| 3,947,581 | 1/1976 | Swered et al. | 424/270 |
| 3,994,772 | 3/1976 | Swered et al. | 162/161 |
| 4,010,277 | 3/1977 | Swered et al. | 424/298 |
| 4,200,633 | 4/1980 | Quinlan | 424/246 |
| 4,200,634 | 4/1980 | Quinlan | 424/246 |
| 4,285,765 | 2/1981 | Pera et al. | 162/161 |
| 4,295,932 | 10/1981 | Pocius | 162/161 |
| 4,411,799 | 8/1983 | Ito et al. | 210/753 |
| 4,451,376 | 4/1984 | Sharp | 210/701 |
| 4,518,610 | 6/1985 | Umekawa et al. | 514/516 |
| 4,539,071 | 3/1985 | Clifford et al. | 162/161 |
| 4,579,665 | 6/1986 | Davis et al. | 210/755 |
| 4,594,091 | 6/1986 | Girvan | 71/67 |
| 4,595,691 | 3/1986 | LaMarre et al. | 514/367 |
| 4,597,940 | 2/1986 | Hager | 422/32 |
| 4,644,021 | 2/1987 | Toda et al. | 523/122 |
| 4,648,978 | 4/1987 | Makinen et al. | 210/759 |
| 4,655,936 | 4/1987 | Stuebner | 210/764 |
| 4,661,503 | 4/1987 | Martin et al. | 514/372 |
| 4,661,517 | 7/1987 | Martin et al. | 514/515 |
| 4,661,518 | 8/1987 | LaMarre et al. | 514/528 |
| 4,684,469 | 7/1987 | Pedersen et al. | 210/632 |
| 4,720,492 | 1/1988 | Quinlan | 514/222 |

OTHER PUBLICATIONS

Du Pont Industrial Chemicals Department Product Data Sheet, "Oxone", Monopersulfate Compound (1985).
Index Guide, Chem. Abst., 1981, p. 1347G, 11th Coll. Index., Chem. Abst., p. 47874GS.
Baldry, Chem. Abst., vol. 102 (1985), 218211B.

*Primary Examiner*—Richard L. Raymond
*Assistant Examiner*—Brian M. Burn
*Attorney, Agent, or Firm*—Birch, Stewart, Kolasch & Birch

[57] ABSTRACT

The present invention is directed to microbiocidal combinations and processes for inhibiting the growth of microorganisms. The novel combinations and processes of the present invention show unexpected activity against microorganisms, including bacteria, fungi and algae. Specifically, the combinations of materials which are to be added to a system at the time of their use comprise (i) an oxidant such as potassium monopersulfate, sodium perborate, hydrogen peroxide or sodium percarbonate, (ii) a microbiocide such as 2,2-dibromo-3-nitrilopropionamide, methylene bis thiocyanate, 5-chloro-2-methyl-4-isothiazolin-3-one/2-methyl-4-isothiazolin-3-one, tetrahydro-3,5-dimethyl-2H,1,3,5-thiadiazine-2-thione, and sodium dimethyldithiocarbamate/disodium ethylene bis dithiocarbamate and optionally (iii) a surfactant such as a fluorinated surfactant, and (iv) an anti-corrosive material such as an anhydrous phosphate, or combinations thereof.

29 Claims, 2 Drawing Sheets $10^3$    $10^4$    $10^5$    $10^6$    $10^7$

MICROBIOCIDAL COMBINATIONS OF MATERIALS AND THEIR USE

FIELD OF THE INVENTION

The present invention relates to microbiocidal combinations of materials and processes utilizing these combinations for inhibiting the growth of microorganisms. More particularly, the combinations of materials which are to be added to a system at the time of their use comprise (i) an oxidant such as potassium monopersulfate, sodium perborate, hydrogen peroxide or sodium percarbonate, (ii) a microbiocide such as 2,2-dibromo-3-nitrilopropionamide, methylene bis thiocyanate, 5-chloro-2-methyl-4-isothiazolin-3-one/2-methyl -4-isothiazolin-3-one, or tetrahydro-3,5-dimethyl-2H,1,3,5-thiadiazine-2-thione, sodium dimethyldithiocarbamate/disodium ethylene bisdithiocarbamate and optionally (iii) a surfactant such as a fluorinated surfactant, sodium and (iv) an anti-corrosive material such as an anhydrous phosphate, or combinations thereof.

BACKGROUND OF THE INVENTION

The formation of slime by microorganisms is a problem which commonly occurs in many systems. For example, slime commonly forms in cooling water systems, lagoons, lakes, ponds, pulp and paper mill systems, petroleum operations and in industrial lubricants and coolants. In cooling systems which employ large amounts of water as the cooling medium, the formation of slime by microorganisms is a significant and constant problem. Problematic microorganisms include bacteria, sulfate reducing bacteria, fungi and algae which produce slime in aqueous systems where such slime is objectionable from either an operational or an aesthetic point of view.

Moreover, airborne microorganisms are readily entrained in water from cooling towers because this medium is an ideal growth environment for microbiocidal growth. Various types of microorganisms flourish in the cooling tower itself while other organisms grow in such areas as the piping, the tower sump and in the passages of the cooling system. Typically, the slime acts to deteriorate towers made of wood or it promotes corrosion when deposited on metal surfaces of cooling systems. Furthermore, the slime tends to plug or foul pipes and valves and to form deposits within heat exchange surfaces thereby reducing heat exchange or cooling efficiency.

Pulp and paper mill systems also operate at conditions which encourage the growth of microorganisms resulting in similar fouling problems discussed hereinabove. Moreover, microorganisms become entrained in the paper product itself causing breakage on the paper machines which necessitates the shutting down of the paper making process. As a result, production time is lost because the equipment must be cleaned and the value of the slime containing product is reduced because of its poor quality.

Slime may also be objectionable from the standpoint of cleanliness and sanitation in breweries, wineries, dairies and other industrial plants or establishments. Moreover, sulfate reducing bacteria may become problematical in waters used for the secondary recovery of petroleum or for oil drilling in general. For example, these organisms are able to reduce sulfates present in the injection water to sulfides which in turn react with soluble iron salts to form insoluble iron sulfide. Matted deposits composed of sulfides, occluded oil and other solids are thereby produced which is undesirable since water containing such deposits when injected underground may plug subterranean formations. In addition, sulfate reducing bacteria cause the corrosion of metal by accelerating galvanic action. Accordingly, microbiological corrosion is a well recognized problem in the petroleum industry.

Moreover, ponds, lakes, lagoons or pools used either for industrial purposes or for pleasure often become suitable environments for microbial growth, especially during warm weather. Health problems including infection may result from the growth of microorganisms in recreational areas. In addition, microorganisms cause further problems during industrial storage and these organisms must be eliminated, for example, prior to use of the stored materials.

In addition, lubricants and cutting fluids are prepared by mixing organic compounds with water to produce solids, emulsions or suspensions in many metal forming operations. Bacteriological contamination of these fluids is inevitable due to the heat and dirt found in many metal working plants. These fluids must be discarded when biological contamination is too severe.

Accordingly, because of the problems discussed hereinabove in various industrial processes, numerous biocidal materials have been recommended in order to eliminate or to reduce microbial growth. Various materials have enjoyed widespread use in such applications including chlorine, chlorine dioxide, organo-mercurials, chlorinated phenols, organo-bromines and various organo-sulfur compounds. However, each of these generally useful materials is deficient for a variety of reasons. For instance, chlorination is limited by its specific toxicity for slime-forming organisms at economic levels by the pH of the aqueous medium and by the ability of chlorine to react before its full biocidal function is achieved.

Moreover, economy is a significant consideration with regard to the use of known biocides. The cost of the biocide and the expense of its applications are examples of the economic factors which must be considered. Typically, the effectiveness of the known biocides is rapidly reduced as a result of exposure to physical conditions such as temperature or a reaction with ingredients in the system which results in a loss of biocidal effectiveness. Therefore multiple doses or large quantities of expensive biocidal chemicals have heretofore been required in order to maintain control over microbial growth.

It is, therefore, a principal object of the present invention to provide microbiocidal combinations of materials which are to be added to a system at the time of their use for controlling the growth of microorganisms.

It is another object of this invention to provide an improved process for controlling microorganisms in aqueous systems such as pulp and paper mill systems, cooling water systems, and petroleum operations.

These and other objects of the novel microbiocidal combinations of materials and processes of using the same of this invention will become apparent and are further described hereinbelow.

SUMMARY OF THE INVENTION

The present invention is directed to combinations of materials which are added to a system at the time of their use and which are used to control or inhibit microbial growth. Specifically, the combinations of the present invention comprise (i) a microbiocidal effective amount of an oxidant such as potassium monopersulfate, sodium perborate, hydrogen peroxide or sodium percarbonate, (ii) a microbiocidal effective amount of a microbiocide such as 2,2-dibromo-3-nitrilopropionamide, methylene bis thiocyanate, 5-chloro-2-methyl-4-isothiazolin-3-one/2-methyl-4-isothiazolin-3-ene, or tetrahydro-3,5-dimethyl-2H,1,3,5-thiadiazine-2-thione, sodium dimethyldithiocarbamate/dissodium and optionally (iii) a surfactant such as a fluorinated surfactant, and (iv) an anti-corrosive material such as an anhydrous phosphate, or combinations thereof.

Furthermore, the combinations of the invention are utilized for controlling the growth and reproduction of microorganisms by adding an effective amount of the combination sufficient to control microbial growth in the system which is treated. The types of systems which are treated to control microbial growth include, but is not limited to, cooling water systems, pulp and paper mill systems, petroleum operations, industrial lubricants and coolants, lagoons, lakes, ponds, etc.

DETAILED DESCRIPTION OF THE INVENTION

Figure 1:
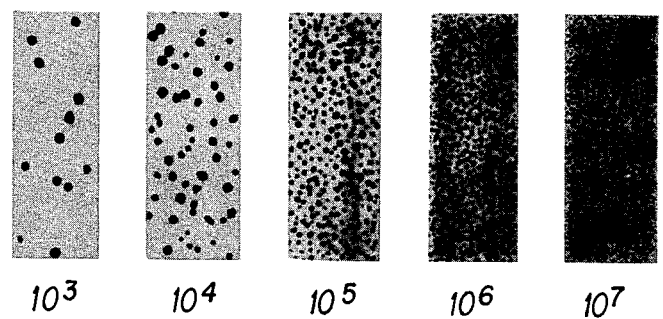
FIG. 1 shows the EASI-CULT TTC model chart for visually estimating the number of cultures (e.g. bacteria/ml)

The foregoing objects are obtained by utilizing combinations of materials which are added to a system at the time of their use and which comprise mixtures of (i) oxidizing agents such as potassium monopersulfate, sodium perborate, hydrogen peroxide or sodium percarbonate, (ii) microbiocides such as 2,2-dibromo-3-nitrilopropionamide (DNP), methylene bis thiocyanate (MBT), 5-chloro-2-methyl-4 -isothiazolin -3-one/2 -methyl-4-isothiazolin-3-one (CMI) or, tetrahydro-3,5-dimethyl -2H,1,3,5-thiadiazine-2-thione, sodium dimethyldithiocarbamate disodium ethylene bis dithiocarbamate (TDD) and optionally (iii) a surfactant such as a fluorinated surfactant, and (iv) an anti-corrosive material such as anhydrous phosphate or combinations thereof. The resulting mixtures unexpectantly have a higher activity than that of the individual components which make up the mixtures.

According to the invention, a system is treated to inhibit the growth of the microorganisms with at least one microbiocide and at least one oxidant. These ingredients are typically added separately as individual compositions or components or they may be added to the system either concurrently or sequentially. The microbiocide is not combined with the oxidant well in advance of being added to the system because these materials adversely react over time when they are brought into direct contact with each other in concentrated form.

The combinations of this invention are utilized for controlling microbrial growth and reproduction in cooling water systems, pulp and paper mill systems, petroleum operations (e.g. oil well applications), industrial lubricants and coolants, lagoons, lakes and ponds, etc. The particular type of microorganisms present in these areas vary from location to location, and even at a given location over a period of time. Representative examples of microorganisms including fungi and bacteria which may be present at a given location and which need to be controlled include such genera as Asperoillus, Penicillium, Candida, Saccharomyces, Aerobacter, Escherichia, Alcaligenes, Bacillus, Chlorella, Spirogyra, Oscillatoria, Vaucheria, Pseudomonas, Salmonella, Staphylococcus, Pallularia, Flavobacterium and Rhizopus. The amount of the active ingredients of the invention which are to be added to these systems should be sufficient to control the microorganisms which are present in the system.

The amount of the microbiocides, the oxidant and optionally the surfactant and/or anti-corrosive material may be varied broadly while maintaining good biological control of such systems as cooling tower systems or paper making systems. For example, the preferable amount of 2,2-dibromo-3-nitrilopropronamide (DNP) in the system may be from about 2.5 ppm to about 10 ppm. In addition, the amount of potassium monopersulfate may be from about 5 ppm to about 60 ppm. However, in general, the amount of microbiocide and oxidant in the system may be between 2.5 ppm and 30 ppm. In addition, an equal amount of oxidant may be combined with the microbiocides (e.g. a 50:50 mix). Moreover, the amount of MBT in the system may be from about 10 ppm to about 45 ppm. When the microbiocides and oxidants are present in the above amounts, the resulting combination possesses a higher degree of effectiveness against microorganisms than the individual components comprising the mixture.

These resulting mixtures possess a high degree of slimicidal activity which could not have been predicted beforehand from the known activity of the individual ingredients comprising the mixture. Accordingly, it is therefore possible to produce a more effective slime-control agent than has previously been available. Because of the enhanced activity of the mixture, the total quantity of the biocide required for an effective treatment may be reduced.

Furthermore, approximately 0.4 grams to approximately 100 grams (about 400 ppm) of surfactant such as a fluorinated surfactant may be optionally added to the system. Suitable fluorinated surfactants include those manufactured by 3M such as FC-99, FC-100 and FC-129. FC-99 is an anionic surfactant which is a 25% active solution of amine-perfluoroalkyl sulfonates in water. FC-100 is an amphoteric surfactant which is a 28% active solution of fluorosurfactant solids in glycol/water. FC-129 is an anionic surfactant which is a 50% solution of potassium fluorinated alkyl carboxylates in water, butyl cellosolve and ethanol. Moreover, surfactants such as the alkylaryl polyether alcohols, polyether alcohols, alkyl benzene sulfonates and sulfates, and the like, may also be employed to enhance the dispersibility and stability of these formulations. In addition, sodium linear dodecyl benzene sulfonate may be a suitable surfactant. Also, a suitable class of surfactants is 0.5-50 ppm of propylene-oxide-ethylene oxide block copolymers which comprises a polyoxy-propylene glycol polymer having a molecular weight of from 1500-2000 which has been reacted with from 5-30% by weight of ethylene oxide. These latter compounds are primarily made by BASF as the Pluronic and Tetronic series. The fluorinated surfactants have been found to be about as effective as the pluronic series.

The invention further envisions the use of an anti-corrosive material as an optional ingredient. For instance, an anhydrous phosphate such as tetrapotassium pyrophosphate may be added to help protect mild steel from corrosive attack by the oxidant (e.g. monopersulfate). The anti-corrosive material may be blended with an oxidant such as OXONE before being added to the system. The anti-corrosive material may be present in an amount of from ½–50% based on the total amount of oxidant and anti-corrosive material in the mixture. More preferably, the amount of the anti-corrosive material is at least 1% of the total amount of oxidant and anti-corrosive material in the mixture. A typical formulation comprises 2% tetrapotassium pyrophosphate and 98% OXONE in order to produce the maximum amount of oxidizing power. Both sodium tripolyphosphate and tetrapotassium pyrophosphate are effective in reducing mild steel corrosion.

As to the amount of the combinations of materials to be added to the various systems, suitable and preferred quantities vary according to the specific system in which the combinations are used. As described above, when added to aqueous systems to control microorganisms, the suitable quantities vary from about 2.5 to 125 ppm of microbiocide to 1 to 125 ppm of oxidizing agent. Larger quantities of the microbiocides or oxidant may be used with no detrimental effect, but such large quantities increase the cost of treatment while having little additional benefit.

The microbiocides used in this invention are commercially available compounds or are easily synthesized from commercially available raw materials. Several representative microbiocides used in the invention and their suppliers are listed below in order of decreasing effectiveness.

The microbiocide, the oxidant and the optional materials may be added to the system sequentially or simultaneously. Moreover, the microbiocide may be metered into the system. In contrast, the solid oxidants, such as OXONE, may be added to the system by hand. Because some users prefer an all liquid system, it is possible to dissolve the solid oxidant in water and to add it to the system as a liquid.

2,2-dibromo-3-nitrilopropionamide (DNP) is a commercially available microbiocide (e.g. LESTER BAC-20), manufactured by Lester Laboratories, Inc., Atlanta, Georgia, or by the Dow Chemical Company of Midland, Michigan, (e.g. Dow XD-7287L).

Methylene bis thiocyanate (MBT), $CH_2(SCN)_2$, may be prepared for example, by the known procedure of reacting methylene bromide or iodide with an alkali metal or ammonium thiocyanate. MBT (e.g. MICROBIOCIDE 10) is a commercially available microbiocide manufactured by Lester Laboratories, Inc.

5-chloro-2-methyl-4-isothiazolin-3-one/2-methyl-4-isothiazol in-3-one (CMI) is a commercially available microbiocide manufactured by Lester Laboratories (e.g. MICROBIOCIDE-76) or by Rohm and Hass (e.g. KATHON 886).

Tetrahydro-3,5-dimethyl-2H,1,3,5-thiadiazine-2-thione (TDD) is a known compound and is commercially available from Lester Laboratories (e.g. MICROBIOCIDE 24) or from Stauffer Chemical (e.g. N-521).

Sodium dimethyldithiocarbamate/sodium ethylene bis dithiocarbamate (SDT) is a known formulation which is commercially available from Lester Laboratories (e.g., LESTER 30) or from VININGS Chemical (e.g., AMA-230).

Examples of microbiocides which did not respond to and were antagonistic to the oxidants tested were quaternary amine compounds such as the alkyl dimethylbenzyl amonium chloride family and (WSCP) poly[oxyethylene (dimethyliminio) ethylene (dimethyliminio) ethylene dichloride].

The oxidants used in the compositions of this invention are also commercially available compounds or are easily synthesized from commercially available raw materials. Several representative oxidizing agents useful in the invention are listed below.

Potassium monopersulfate is the most preferred oxidizing agent and is a known compound which is commercially available from DuPont as OXONE.

Additional oxidizing agents which are used in accordance with the present invention are sodium perborate, hydrogen peroxide and sodium percarbonate. Although the abovementioned oxidizing agents are preferred, a number of other oxidizing agents including potassium permanganate, sodium or ammonium persulfate and diperoxydodecanedoic acid may be used.

Suitable microbiocides and/or oxidants of this invention may be used diluted with a suitable solid or liquid carrier. Dusts may be prepared with a finely divided solid including talc, clay, pyrophyllite, diatomaceous earth, hydrated silica, calcium silicate, or magnesium carbonate. Moreover, wetting and/or dispersing agents may optionally be used. A wettable powder results when the proportions of these materials are increased which may be dispersed in water and applied from a spray.

Dusts may typically contain 1 to 15 percent of the microbiocides of this invention, while wettable powders may contain up to 50 percent or more of these compounds.

A typical formulation of a wettable powder comprises 20 percent to 50 percent of the suitable compounds of this invention, 45 percent to 75 percent of one or more finely divided solids, one percent to five percent of a wetting agent, and one percent to five percent of a dispersing agent. Typical wetting agents include sodium dodecyl sulfate, sodium nonylbenzene sulfonate, sodium dioctyl sulfosuccinate, octylphenoxypolyethoxyethanol, or other nonionic agents, such as ethylene and/or propylene oxide condensates with long chained alcohols, mercaptans, amines, or carboxylic acids. Typical dispersing agents include the sodium sulfonate of condensed napthalene-formaldehyde and lignin sulfonates.

Liquid concentrates may also be used. These are prepared by taking up the microbiocides of this invention in an organic solvent together with one or more surface active agents.

The microbiocides used in the present invention may be used in conjunction with other microbicidal agents and also in conjunction with miticides or insecticides or other pesticides.

The present invention is now described in greater detail by reference to the following examples which are given here for illustrative purposes only, and are not intended to limit the scope of the invention.

EXAMPLES

Test Procedure 1: Laboratory Tests

EASICULT-TTC test strips were used to evaluate the "kill power" of the various microbiocidal systems which were tested. EASICULT-TTC test strips are commercially available (Medical Technology Corp., Somerset, N.J.) and are culture paddles which are dipped into a solution containing various microorganisms. The strips which have been dipped are closed within a container or vial and they are then incubated for 24 to 48 hours in an oven kept at a temperature range of 30°–40° C. The number of cultures (e.g. bacteria/ml) can be visually estimated from the EASICULT TTC model chart as shown in FIG. 1.

More specifically, for each test one four ounce sample jar and one EASICULT-TTC test strip is used. The test samples comprise about 1 ml to 100 ml of the solution to be tested. For example, about 100 ml of a sample is dosed at 30 ppm of a microbiocide such as MBT. If 1 ml were to have such a dose, it would mean that the original solution was 100 times as concentrated (e.g. 3000 ppm). This is equivalent to adding 3 grams of microbiocide to 1 liter of water. The proper amount of microbiocide is then added to the sample jar (e.g. 1 ml in the above example). The sample jar is then topped off with 100 grams of 1–10% of a suitable sample to be tested and is allowed to sit for 45 minutes in contact with the microbiocide/oxidant treatment, if any. After 45 minutes, an EASICULT-TTC test strip (e.g. paddle) is dipped into the prepared microbe/microbiocide solution and stirred for five complete circles in the jar. The paddle is withdrawn and tapped five times on the side of the jar to remove excess moisture. The paddle is replaced into its container which is then closed. The EASICULT-TTC unit is then incubated for 24–48 hours. At the end of this period the test strip is removed from incubation and is evaluated in the manner described by the EASICULT-TTC manufacturer. This procedure allows the number of cultures to be conveniently determined.

The microbial samples to be tested may be prepared as follows. For example, 1 gram of cooling tower slat scrapings is obtained from a cooling tower. In a 1 gram jug add 5 grams fructose and 5 grams of dehydrated culture broth to the scrapings. The jug is then topped off with deionized water. The sample to be tested is then allowed to grow for at least one week before use.

Test Procedure 2: Field Tests

The procedure for conducting field tests is to sample the actual test site (e.g. an air washer sump) with an EASICULT-TTC test strip 30 minutes before any chemicals are added. The microbiocide (e.g. CMI) is added to the test site (e.g. air washer sump) in a prespecified amount (e.g. 125 ppm). A prespecified amount of oxidant (e.g. OXONE) and optionally anti-corrosive material (e.g. phosphate) is then added. Preferably, an equivalent amount of P-3 (Oxone and phosphate) is used. EASICULT-TTC test strips are then used to sample the test site for a predetermined period (e.g. every half hour for four hours after adding the chemicals). Then, the test site is tested after longer intervals, for example, after eight hour periods.

EXAMPLE 1

Microbiocide tetrahydro-3,5-dimethyl-2H,1,3,5-thiadiazine-2-thione (MICROBIOCIDE 24) was evaluated using Test Procedure 1 to determine the effect when combined with microbiocide Poly(oxyethylene(dimethylimino)-ethylene-(dimethylimino) -ethylene dichloride) (e.g. ALGAECIDE 15) or with the oxidizing agent sodium perborate, or combinations thereof. The sample tested was taken from a waste water treatment plant of a specialty metal fabricating plant located in Carrollton, Georgia. The effectiveness of the various combinations is shown below in Table I.

TABLE I

| Combinations of MicroBiocides and Oxidants Against Bacteria | | | |
|---|---|---|---|
| Treatment | Ratio (a/b) | Treatment Level (ppm) | EASICULT Test Results (bacteria/ml) |
| Control | 0/0 | 0 | $10^4$ |
| a: MICROBIOCIDE 24/ b: Sodium Perborate | 13/87 | 75/500 | 0 |
| a: MICROBIOCIDE 24/ b: ALGAECIDE 15 | 43/57 | 75/100 | $10^2$–$10^3$ |
| a: MICROBIOCIDE 24/ b: — | 100/0 | 75/0 | $10^3$ |

The results show the improved effectiveness of MICROBIOCIDE 24 when used in combination with sodium perborate as the oxidizing agent. The oxidizing agent was more helpful than another known biocide.

EXAMPLE 2

Microbiocide 5-chloro-2-methyl-4-isothiazolin-3-one/2-methyl -4-isothiazolin-3-one (MICROBIOCIDE 76) was evaluated using Test Procedure 1 to determine the effect when combined with the oxidizing agent potassium mo (OXONE). The effect of combining SURFACTANT AEROSOL MA-80 with the oxidizing agent potassium monopersulfate (OXONE) was also evaluated. The sample tested was taken from a waste water treatment plant of a specialty metal fabricating plant in Carrollton, Georgia. The effectiveness of the various combinations is shown below in Table II.

TABLE II

| Combinations of Microbiocides and Oxidants Against Bacteria | | | |
|---|---|---|---|
| Treatment | Ratio (a/b) | Treatment Level (ppm) | EASICULT Test Results (bacteria/ml) |
| a: MICROBIOCIDE 76 b: — | 100/0 | 20/0 | $10^5$ |
| a: MICROBIOCIDE 76/ b: OXONE | 50/50 | 20/20 | $10^2$ |
| a: AEROSOL MA-80/ b: OXONE | 50/50 | 20/20 | $10^4$ |

The results show that the oxidizing agent potassium monopersulfate (OXONE) combined with the microbiocide was more effective than when combined with the surfactant (dispersant).

EXAMPLE 3

Microbiocides 5-chloro-2-methyl-4-isothiazolin-3-one/2-methyl-4-isothiazolin-3-one (MICROBIOCIDE 76) and methylene bisthiocyanate (MICROBIOCIDE 10) were evaluated using Test Procedure 1 to determine the effect when combined with surfactant AEROSOL OT-75, oxidizing agent potassium monopersulfate (OXONE), or with a combination thereof. The sample tested was taken from a waste water treatment plant of a specialty metal fabricating plant in Carrollton, Georgia. The effectiveness of the various combinations are shown below in Table III.

TABLE III

Combinations of Microbiocides and Oxidants Against Bacteria

| Treatment | Ratio (a/b/c) | Treatment Level (ppm) | EASICULT Test Results (bacteria/ml) |
|---|---|---|---|
| Control | 0/0/0 | 0/0/0 | $10^4$ |
| a: MICROBIOCIDE 76<br>b: —<br>c: — | 100/0/0 | 60/0/0 | $10^3$ |
| a: MICROBIOCIDE 76<br>b: AEROSOL OT-75<br>c: — | 50/50/0 | 60/60/0 | $10^3$ |
| a: MICROBIOCIDE 76<br>b: —<br>c: OXONE | 50/0/50 | 60/0/60 | 0 |
| a: MICROBIOCIDE 76<br>b: AEROSOL OT-75<br>c: OXONE | 33/33/33 | 60/60/60 | 0 |
| a: MICROBIOCIDE 10<br>b: —<br>c: — | 100/0/0 | 60/0/0 | $10^4$ |
| a: MICROBIOCIDE 10<br>b: AEROSOL OT-75<br>c: — | 50/50/0 | 60/60/0 | $10^3$–$10^4$ |
| a: MICROBIOCIDE 10<br>b: —<br>c: OXONE | 50/0/50 | 60/0/60 | 0 |
| a: MICROBIOCIDE 10<br>b: AEROSOL OT-75<br>c: OXONE | 33/33/33 | 60/60/60 | 0 |

The results show the improved effectiveness of microbiocides MICROBIOCIDE 76 and MICROBIOCIDE 10 when used in combination with oxidizing agent potassium monopersulfate (OXONE) and optionally a surfactant (AEROSOL OT-75). Whereas the impact of the surfactant was marginal, the impact of the oxidizing agent (OXONE) combined with the microbiocides was dramatically more effective.

EXAMPLE 4

The effectiveness of the microbiocide methylene bis thiocyanate (MICROBIOCIDE 10) was evaluated using Test Procedure 1 to further evaluate the effect when combined with oxidizing agent potassium monopersulfate (OXONE) and optionally with surfactant (AEROSOL OT-75). The sample tested was taken from an air washer in a textile mill located in Talladega, Alabama. The effectiveness of the various combinations are shown below in Table IV.

TABLE IV

Combinations of Microbiocides and Oxidants Against Bacteria

| Treatment | Ratio (a/b/c) | Treatment Level (ppm) | EASICULT Test Results (bacteria/ml) |
|---|---|---|---|
| Control | 0/0/0 | 0 | $10^5$ |
| a: MICROBIOCIDE 10<br>b: OXONE<br>c: — | 50/50/0 | 30/30/0 | 0 |
| a: MICROBIOCIDE 10<br>b: OXONE<br>c: AEROSOL-OT-75 | 33/33/33 | 30/30/30 | 0 |
| a: MICROBIOCIDE 10<br>b: OXONE<br>c: — | 50/50/0 | 45/45/0 | 0 |
| a: MICROBIOCIDE 10<br>b: OXONE<br>c: — | 50/50/0 | 15/15/0 | $10^1$ |

The results show that the use of the oxidant allows complete kill of the organisms at a fraction of the normal dosage level (30 ppm).

EXAMPLE 5

Microbiocide methylene bis thiocyanate (MICROBIOCIDE 10) was further evaluated using Test Procedure 1 to determine the extent of the effect when combined with oxidizing agent potassium monopersulfate (OXONE) and optionally with AEROSOL-OT-75. The sample tested was taken from an air washer in a textile mill located in Talladega, Alabama. The effectiveness of the various combinations are shown below in Table V.

TABLE V

Combinations of Microbiocides and Oxidants Against Bacteria

| Treatment | Ratio (a/b/c) | Treatment Level (ppm) | EASICULT Test Results |
|---|---|---|---|
| Control | 0/0/0 | 0 | $10^5$ |
| a: MICROBIOCIDE 10<br>b: OXONE<br>c: — | 50/50/0 | 5/5/0 | $10^5$ |
| a: MICROBIOCIDE 10<br>b: OXONE<br>c: AEROSOL-OT-75 | 33/33/33 | 10/10/10 | $10^1$ |
| a: MICROBIOCIDE 10<br>b: OXONE<br>c: AEROSOL-OT-75 | 33/33/33 | 15/15/15 | 0 |

The results show the improved effectiveness of MICROBIOCIDE 10 when used in combination with oxidizing agent potassium monopersulfate (OXONE) and optionally with AEROSOL OT-75.

EXAMPLE 6

Microbiocide methylene bis thiocyanate (MICROBIOCIDE 10) was again evaluated using Test Procedure 1 to determine the extent of the effect when combined with oxidizing agent potassium monopersulfate (OXONE). However, in these tests, a more potent or virulent selection of microorganisms was utilized. The sample tested was taken from an air washer in a textile mill located in Mission Valley, Texas. The effectiveness of the various combinations are shown below in Table VI.

TABLE VI

Combinations of Microbiocides and Oxidants Against Bacteria

| Treatment | Ratio (a/b) | Treatment Level (ppm) | EASICULT Test Results (bacteria/ml) |
|---|---|---|---|
| Control | 0/0 | 0 | $10^7$ |
| a: MICROBIOCIDE 10<br>b: OXONE | 33/67 | 30/60 | $10^4$ |
| a: MICROBIOCIDE 10<br>b: OXONE | 40/60 | 30/45 | $10^4$ |
| a: MICROBIOCIDE 10<br>b: OXONE | 50/50 | 30/30 | $10^5$ |
| a: MICROBIOCIDE 10 | 67/33 | 30/15 | $10^7$ |

TABLE VI-continued

Combinations of Microbiocides and Oxidants Against Bacteria

| Treatment | Ratio (a/b) | Treatment Level (ppm) | EASICULT Test Results (bacteria/ml) |
|---|---|---|---|
| b: OXONE | | | |
| a: MICROBIOCIDE 10 | 75/25 | 30/10 | $10^7$ |
| b: OXONE | | | |

The above results show effective concentrations of the various MICROBIOCIDE/OXONE combinations on the specific samples tested.

EXAMPLE 7

The effectiveness of microbiocide methylene bis thiocyanate (MICROBIOCIDE 10) was further evaluated using Test Procedure 1 to determine the extent of the effect when combined with oxidizing agent potassium monopersulfate (OXONE). However, in these tests the microorganisms were obtained from the textile mill in Talladega, Alabama. The effectiveness of the various combinations are shown below in Table VII.

TABLE VII

Combinations of Microbiocides and Oxidants Against Bacteria

| Treatment | Ratio (a/b) | Treatment Level (ppm) | EASICULT Test Results (bacteria/ml) |
|---|---|---|---|
| Control | 0/0 | 0 | $10^6$ |
| a: MICROBIOCIDE 10 | 50/50 | 30/30 | 0 |
| b: OXONE | | | |

EXAMPLE VIII

Microbiocides methylene bis thiocyanate (MICROBIOCIDE 10) and 2,2-dibromo-3-nitrilopropionamide (LESTER BAC-20) were evaluated using Test Procedure I to determine the effect when combined with oxidizing agents hydrogen peroxide (e.g. 8% $H_2O_2$), potassium monopersulfate (OXONE) and with the surfactant ZONYL FSJ (DuPont). The samples tested were taken from an air washer in effectiveness of the various combinations are shown below in Table VIII.

TABLE VIII

Combinations of Microbiocides and Oxidants Against Bacteria

| Treatment | Ratio (a/b/c) | Treatment Level (ppm) | EASICULT Test Results (bacteria/ml) |
|---|---|---|---|
| Control | 0/0/0 | 0 | $10^6$ |
| a: MICROBIOCIDE 10 | 100/0/0 | 10/0/0 | $10^4$ |
| b: — | | | |
| c: — | | | |
| a: MICROBIOCIDE 10 | 91/9/0 | 10/1/0 | $10^4$ |
| b: 8% $H_2O_2$ | | | |
| c: — | | | |
| a: MICROBIOCIDE 10 | 66/33/0 | 10/5/0 | $10^3$ |
| b: 8% $H_2O_2$ | | | |
| c: — | | | |
| a: MICROBIOCIDE 10 | 50/25/25 | 10/5/5 | $10^3$ |
| b: 8% $H_2O_2$ | | | |
| c: ZOYNL FSJ | | | |
| a: MICROBIOCIDE 10 | 50/50/0 | 10/10/0 | $10^3$ |
| b: 8% $H_2O_2$ | | | |
| c: — | | | |
| a: BAC-20 | 66/33/0 | 10/5/0 | $10^1$ |
| b: 8% $H_2O_2$ | | | |
| c: — | | | |
| a: BAC-20 | 50/50/0 | 10/10/0 | 0 |
| b: 8% $H_2O_2$ | | | |

TABLE VIII-continued

Combinations of Microbiocides and Oxidants Against Bacteria

| Treatment | Ratio (a/b/c) | Treatment Level (ppm) | EASICULT Test Results (bacteria/ml) |
|---|---|---|---|
| c: — | | | |
| a: MICROBIOCIDE 10 | 40/60/0 | 10/15/0 | $10^3$ |
| b: OXONE | | | |
| c: — | | | |
| a: BAC-20 | 40/60/0 | 10/15/0 | 0 |
| b: OXONE | | | |
| c: — | | | |

These results show the improved effectiveness of microbiocides MICROBIOCIDE 10 and LESTER BAC-20 when used in combination with oxidizing agent hydrogen peroxide (e.g. 8% $H_2O_2$) or potassium monopersulfate (OXONE). Moreover, these results demonstrate that the combination of LESTER BAC-20 with each of the oxidizing agents is more effective than the respective combinations with MICROBIOCIDE 10. In other words, the combination of materials utilizing LESTER BAC-20 appears to be superior to the combination of materials using MICROBIOCIDE 10.

EXAMPLE IX

Microbiocides 5-chloro-2-methyl-4-isothiazolin-3-one/2-methyl-4-isothiazolin-3-one (MICROBIOCIDE 76), methylene bis thiocyanate (MICROBIOCIDE 10), and 2,2-dibromo-3-nitrilopropionamide (LESTER BAC-20) were evaluated using Test Procedure 1 to determine the effect when combined with oxidizing agent hydrogen peroxide (e.g. 8% $H_2O_2$) and optionally the surfactant ZONYL. The test samples were taken from an air washer in a textile mill located in Mission Valley, Texas. The effectiveness of the various combinations are shown below in Table X.

TABLE X

Combinations of Microbiocides and Oxidants Against Bacteria

| Treatment | Ratio (a/b/c) | Treatment Level (ppm) | EASICULT Test Results (bacteria/ml) |
|---|---|---|---|
| Control | 0/0/0 | 0 | $10^4$ |
| a: MICROBIOCIDE 76 | 60/20/20 | 30/10/10 | $10^4$ |
| b: ZONYL | | | |
| c: 8% $H_2O_2$ | | | |
| a: MICROBIOCIDE 76 | 33/33/33 | 10/10/10 | $10^5$ |
| b: ZONYL | | | |
| c: 8% $H_2O_2$ | | | |
| a: MICROBIOCIDE 10 | 50/0/50 | 10/0/10 | $10^4$ |
| b: — | | | |
| c: 8% $H_2O_2$ | | | |
| a: BAC-20 | 33/0/66 | 5/0/10 | $10^2$ |
| b: — | | | |
| c: 8% $H_2O_2$ | | | |

These results demonstrate that the combination of LESTER BAC-20 with 8% $H_2O_2$ is superior to the combination of the other materials tested with 8% $H_2O_2$.

EXAMPLE XI

Microbiocide 5-chloro-2-methyl-4-isothiazolin-3-one-2/methyl-4-isothiazolin-3-one (MICROBIOCIDE 76) was further evaluated using Test Procedure 1 to determine the effect when it was combined with oxidizing agents potassium monopersulfate (OXONE), hydrogen peroxide (e.g. 6% $H_2O_2$), sodium perborate, potassium permanganate or sodium percarbonate or with MICROBIOCIDE 80. The samples tested were taken from a cooling tower at Lester Laboratories in East Point, Georgia. The effectiveness of the various combinations are shown below in Table XI.

TABLE XI

Combinations of Microbiocides and Oxidants Against Bacteria

| Treatment | Ratio (a/b) | Treatment Level (ppm) | EASICULT Test Results (bacteria/ml) |
|---|---|---|---|
| Control | 0/0 | 0 | $10^7$ |
| a: MICROBIOCIDE 76<br>b: — | 100/0 | 30/0 | $10^7$ |
| a: MICROBIOCIDE 76<br>b: OXONE | 50/50 | 30/30 | $10^3$ |
| a: MICROBIOCIDE 76<br>b: 6% $H_2O_2$ | 50/50 | 30/30 | $10^6$ |
| a: MICROBIOCIDE 76<br>b: Sodium Perborate | 50/50 | 30/30 | $10^6$ |
| a: MICROBIOCIDE 76<br>b: MICROBIOCIDE 80 | 50/50 | 30/30 | 0 |
| a: MICROBIOCIDE 76<br>b: KBr-Sodium Perborate | 50/50 | 30/30 | $10^5$ |
| a: MICROBIOCIDE 76<br>b: Potassium Permanganate | 50/50 | 30/30 | 0 |
| a: MICROBIOCIDE 76<br>b: Sodium Percarbonate | 50/50 | 30/30 | $10^5$ |

These results demonstrate the relative effectiveness of the various oxidizing agents when compared in use with a constant quantity of the microbiocide (MB-76). The combination of MICROBIOCIDE 76 with MICROBIOCIDE 80, a chlorinating agent, and potassium permanganate were effective for killing completely the bacteria. However, many of these alternate oxidants have intrinsic disadvantages including color, insoluble reaction products and corrosive tendencies.

EXAMPLE XII

Figure 2:
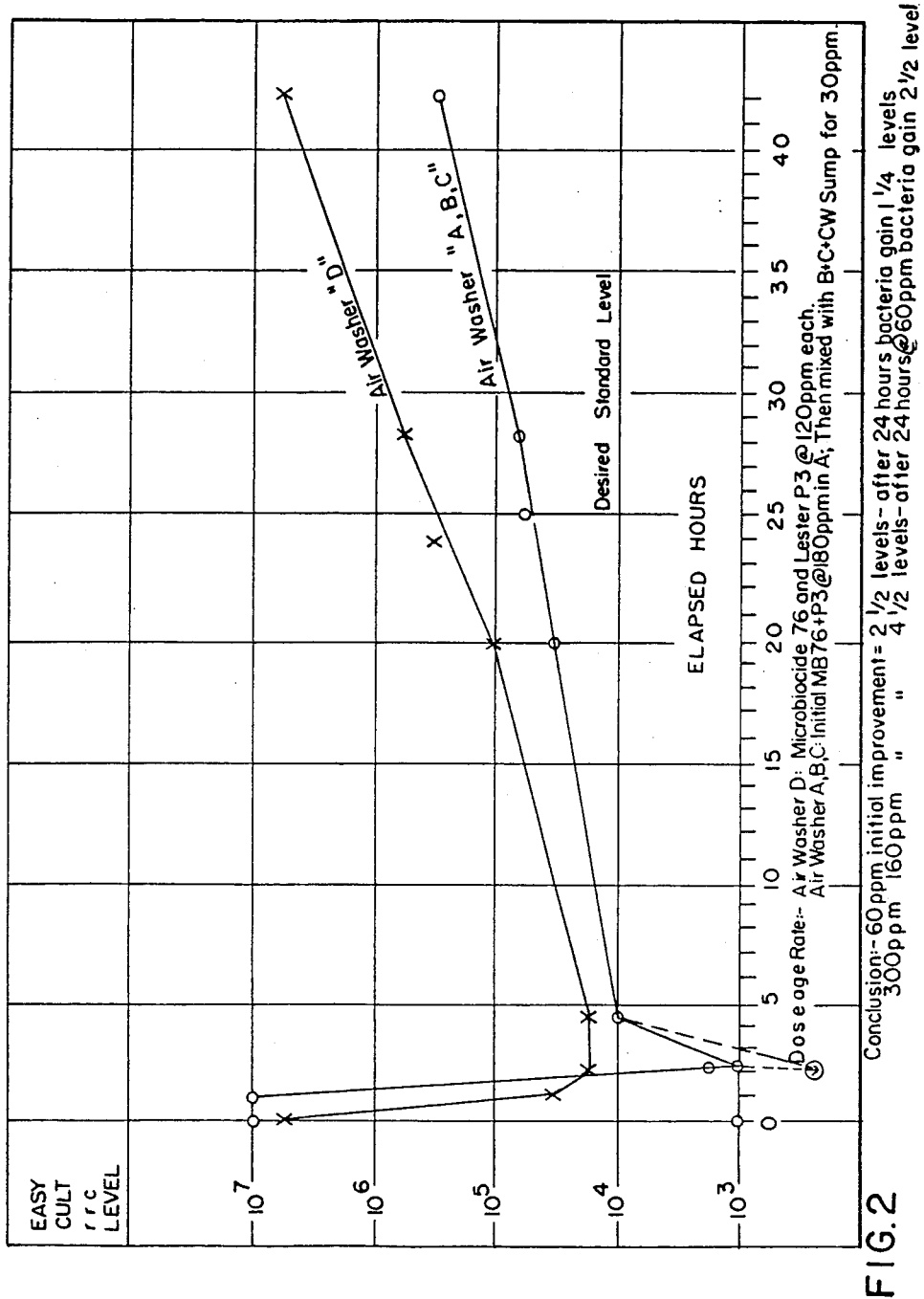
FIG. 2 is a graph of EASI-CULT TTC level versus Time in hours.

A field test was conducted in accordance with Test Procedure 2 at the West Point Pepperell Mission Valley Mill in Texas. An air washer sump was sampled with an EASICULT-TTC test strip 30 minutes before any chemicals were added. MICROBIOCIDE 76 was added to the air washer sump to 125 ppm, followed by an equivalent amount of P-3(OXONE and phosphate). EASICULT-TTC strips were then dipped each half hour for four hours after the chemicals were added. Then, an interval of eight hours passed before another EASICULT-TTC test strip was used, followed by another eight hour interval before dipping another test strip. The initial EASICULT-TTC reading was $10^7$. After about 2.53 hours the reading was reduced to $10^3$. The results are plotted in FIG. 2.

EXAMPLE XIII

In order to establish the effectiveness of the combination in combatting or controlling slime formation which is experienced in various paper and pulp mills, the combinations of the invention are tested in the apparatus of a paper mill. Actual water samples are taken from pulp and paper mill systems which experience slime problems due to the microorganism population of the water. These slime problems are generally caused by a combination of microorganisms, which although primarily bacteria and fungi, in some cases also includes algae. As would be expected, the inventive combinations are added to the cooling water or the pulp and paper mill systems at any convenient point. The combinations are added upstream from the point or points at which microorganism control is desired in once-through or non-circulating systems. In circulating systems or pulp and paper systems, the combinations are added at any point, provided the time lapse and the conditions experienced between the point of addition and the point at which the effect of the combinations are experienced is not so drastic as to result in the neutralization of the effect of the combinations. The samples test at various points in the system and are evaluated as in Test Procedure 2 and should establish the properties of the combination at specific treatment levels to inhibit the growth of microorganisms of the sample tested.

EXAMPLE XIV

In order to ascertain whether the inventive combinations are effective in controlling fungi, evaluations are made following the procedure described by Shema et al, "JOURNAL FOR THE TECHNICAL ASSOCIATION OF THE PULP AND PAPER INDUSTRY." 36, 20A-30A, 1953. The procedure described generally entails incorporating the biocide under test in a nutrient substrate such as agar, malt, etc. and pouring the resulting medium in a Petri dish and allowing the medium to solidify. A button of fungus inoculum is placed on the surface of the solidified medium and the medium is incubated for a period of 14 days. After the period, the diameter of the colony is measured and compared with the diameter of the button of inoculum originally placed upon the surface. If there is no increase in the diameter, the growth of the fungus is considered to be completely inhibited and the treatment level which effectuates this is considered the inhibitory concentration.

The fungi species which is utilized as the test microorganism to evaluate the efficacy of the present combinations are *Penicillium expansum* and *Aspergillus niger*. The study should reveal that the combination of this invention inhibits the growth of *Penicillium expansum* and of *Aspergillus niger*.

EXAMPLE XV

A field test is conducted as in Example XII except a cooling tower is sampled.

EXAMPLE XVI

The effectiveness of the oxidizing agent potassium monopersulfate (OXONE) in combination with several microbiocides is actually unexpected in nature, as shown by the following tests with a sample of microorganisms taken from an air washer in a textile mill located in Talladega, Alabama.

TABLE XVI

Study for combinations of microbiocides and OXIDANTS AGAINST BACTERIA.

| TREATMENT | RATIO | TREATMENT LEVEL | EASICULT TEST RESULTS (bacteria/ml) |
|---|---|---|---|
| Control | 0/0 | 0 | $10^6$ |
| a: BAC-20 : OXONE | 100/0 | 10/0 | $10^2$ |
| b: BAC-20 : OXONE | 0/100 | 0/10 | $10^3$ |
| c: BAC-20 : OXONE | 50/50 | 5/5 | $10^1$ |

The above results show unexpected behavior in that the 50/50 weight mixture of BAC-20 and OXONE showed a greater kill than an equal weight of either the Microbiocide (BAC-20) or the oxidant OXONE by itself.

Similarly, in the same test designed to establish a range of effective combinations of MICROBIOCIDE 76 and OXONE we show the following results:

| | | | |
|---|---|---|---|
| d: MICROBIOCIDE 76 : OXONE | 100/0 | 40/0 | $5 \times 10^5$ |
| e: MICROBIOCIDE 76 : OXONE | 90/10 | 36/2 | $5 \times 10^5$ |
| f: MICROBIOCIDE 76 : OXONE | 75/25 | 30/5 | $10^3$ |
| g: MICROBIOCIDE 76 : OXONE | 50/50 | 20/10 | $10^3$ |
| h: MICROBIOCIDE 76 : OXONE | 25/75 | 10/15 | $10^4$ |
| i: MICROBIOCIDE 76 : OXONE | 10/90 | 4/18 | $5 \times 10^5$ |
| j: MICROBIOCIDE 76 : OXONE | 0/100 | 0/20 | $5 \times 10^5$ |

In the above series, "d" through "j", the ratio is the percent of effective concentration of the MICROBIOCIDE 76 and OXONE respectively. Tests "f" and "g" in which the Microbiocide and oxidant were combined in less than the effective concentration of either shows the combination as being more effective than either component alone (see "d" and "j").

The invention being thus described, it will be obvious that the same may be varied in many ways. Such variations are not to be regarded as a departure from the spirit and scope of the present invention, and all such modifications as in the art are intended to be included within the scope of the following claims.

What is claimed is:

1. A microbiocidal combination of materials to be added to a system at the time of use comprising:
   (i) a microbiocidally effective amount of an oxidant for inhibiting the growth of microorganisms selected from the group consisting of potassium monopersulfate, sodium perborate, hydrogen peroxide and sodium percarbonate, and
   (ii) a microbiocidally effective amount of microbicide for inhibiting the growth of microorganisms selected from the group consisting of 2,2-dibromo-3-nitrilopropion- amide, methylene bis thiocyanate, 5-chloro-2-methyl-4-isothiazolin-3-one/2-methyl-4-iosthiazolin-3-one, tetrahydro-3, 5,-dimethyl-2H,1,3,5-thiadiazine-2-thione, and sodium dimethyldithiocarbamate/disodium ethylene bis dithiocarbmate.

2. A method of controlling the growth and deposition of slime-forming organisms in flowing water systems which comprises adding to the flowing water in said flowing water system the combination as defined in claim 1.

3. A method of controlling the growth and deposition of algae in flowing water systems which comprises adding to the flowing water in said flowing water system the combination as defined in claim 1.

4. A method of controlling the growth and deposition of slime-forming organisms in aqueous systems which comprises adding to said aqueous systems the combination as defined in claim 1.

5. A method of controlling slime in pulp and paper mill water systems which comprises adding to said water systems the combination as defined in claim 1.

6. A method of controlling the growth and proliferation of sulfate reducing bacteria as well as species of slime forming microorganisms in petroleum operation systems, which comprises adding to said petroleum operation systems the combination as defined in claim 1.

7. A method of controlling the growth and proliferation of algae, bacteria, and fungi in fresh water which comprises adding to said fresh water the combination as defined in claim 1.

8. A method of controlling the growth and profileration of algae, bacteria and fungi in cooling water which comprises adding to said cooling water the combination as defined in claim 1.

9. A method of controlling the growth and deposition of slime forming microorganisms in water which comprises adding to the water:
   (i) a microbiocidally effective amount of an oxidant for inhibiting the growth of microorganisms selected from the group consisting of potassium monopersulfate, sodium perborate, hydrogen peroxide and sodium percarbonate, and
   (ii) a microbiocidally effective amount of a microbicide for inhibiting the growth of microorganisms selected from the group consisting of 2,2-dibromo-3-nitrilopropion- amide, methylene bis thiocyanate, 5-chloro-2-methyl-4-isothiazolin-3-one/2-methyl-4-isothiazolin-3-one, tetrahydro-3, 5,dimethyl-2H,1,3,5-thiadiazine-2-thione and sodium dimethyldithiocarbamate/disodium ethylene bis dithiocarbamate.

10. The method of claim 9, comprising a ratio of at least 10 parts of the microbiocide and 90 parts by weight of the oxidant to 90 parts by weight of the microbiocide/10 parts by weight of the oxidant.

11. A microbiocidal combination of materials to be added to a system at the time of use comprising:
   (i) a microbiocidally effective amount of an oxidant for inhibiting the growth of microorganisms selected from the group consisting of potassium monopersulfate, sodium perborate, hydrogen peroxide and sodium percarbonate,
   (ii) a microbiocidally effective amount of a microbicide for inhibiting the growth of microorganisms selected from the group consisting of 2,2-dibromo-3-nitrilopropion- amide, methylene bis thiocyanate, 5-chloro-2-methyl-4-isothiazolin-3-one/2-methyl-4-isothiazoline-3-one, tetrahydro-3, 5,dimethyl-2H,1,3,5-thiadiazine-2-thione, and sodium dimethyldithiocarbamate/disodium ethylene bis dithiocarbamate, and
   (ii) a surfactant.

12. The combination of claim 11, comprising:
   (i) at least 5 ppm of said oxidant
   (ii) at least 2.5 ppm of said microbiocide, and
   (iii) about 400 ppm of said surfactant.

13. The combination of claim 11, comprising 2.5 ppm to 45 ppm of said oxidant and 2.5 ppm to 45 ppm of said microbiocide.

14. The combination of claim 11, wherein the surfactant is a fluorinated surfactant.

15. The combination of claim 11, further comprising an anti-corrosive material.

16. The combination of claim 15, wherein the anti-corrosive material is tetrapotassium pyrophosphate or sodium tripolyphosphate.

17. The combination of claim 1, wherein said oxidant of group (i) is selected from the group consisting of potassium monopersulfate, sodium perborate, hydrogen peroxide and sodium percarbonate, and said microbiocide of group (ii) is 2,2-dibromo-3-nitrilopropionamide.

18. The combination of claim 1, wherein said oxidant of group (i) is potassium monopersulfate and said microbiocide of group (ii) is 5-chloro-2-methyl-4-isothiazolin-3-one/2-methyl-4-isothiazolin-3-one.

19. The combination of claim 1, wherein said oxidant of group (i) is hydrogen peroxide and said microbiocide of group (ii) is methylene bis thiocyanate.

20. The combination of claim 1, wherein said oxidant of group (i) is hydrogen peroxide and said microbiocide of group (ii) is tetrahydro-3-,5-dimethyl-2 H, 1, 3, 5-thiadiazine-2-thione.

21. The combination of claim 1, wherein said oxidant of group (i) is sodium percarbonate and said microbiocide of group (ii) is 5-chloro-2-methyl-4-isothiazolin-3-one/2-methyl-4-isothiazolin-3-one.

22. A microbiocidal combination of materials to be added to a system at the time of use comprising a ratio of at least 10 parts of microbiocide and 90 parts by weight of oxidant to 90 parts by weight of microbiocide to 10 parts by weight of oxidant, wherein:
   (i) said oxidant is selected from the group consisting of potassium monopersulfate, sodium perborate, hydrogen peroxide and sodium percarbonate, and
   (ii) said microbiocide is selected from the group consisting of 2,2-dibromo-3-nitrilopropionamide, methylene bis thiocyanate, 5-chloro-2-methyl-4-isothiazolin-3-one/2-methyl-4-isothiazolin-3-one, tetrahydro-3,5,dimethyl-2H,1,3,5-thiadiazine-2-thione, and sodium dimethyldithiocarbamate/disodium ethylene bis dithiocarbamate.

23. A method of controlling the growth and deposition of algae, bacteria and fungi in a swimming pool which comprises adding to said pool the combination as defined in claim 1.

24. The combination of claim 1, wherein said oxidant of group (i) is OXONE.

25. The combination of claim 1, wherein said oxidant of group (i) is hydrogen peroxide and said microbiocide of group (ii) is sodium dimethyldithiocarbamate/disodium ethylene bis dithiocarbamate.

26. A method of controlling the growth and deposition of slime forming microorganisms in water which comprises adding to the water:
   a microbiocidally effective amount of an oxidant for inhibiting the growth of microorganisms selected from the group consisting of potassium monopersulfate, sodium perborate, hydrogen peroxide and sodium percarbonate, and
   a microbiocidally effective amount of a microbicide for inhibiting the growth of microorganisms.

27. A microbiocidal combination of materials to be added to a system at the time of use comprising:
   a microbiocidally effective amount of an oxidant for inhibiting the growth of microorganisms selected from the group consisting of potassium monopersulfate, sodium perborate, hydrogen peroxide and sodium percarbonate, and
   a microbiocidally effective amount of a microbicide for inhibiting the growth of microorganisms.

28. A method of controlling the growth and deposition of slime forming microorganisms in water which comprises adding to the water:
   a microbiocidally effective amount of an oxidant capable of releasing nascent oxygen for inhibiting the growth of microorganisms, and
   a microbiocidally effective amount of a microbicide for inhibiting the growth of microorganisms.

29. A microbiocidal combination of materials to be added to a system at the time of use comprising:
   a microbiocidally effective amount of an oxidant capable of releasing nascent oxygen for inhibiting the growth of microorganisms, and
   a microbiocidally effective amount of a microbicide for inhibiting the growth of microorganisms.

* * * * *